United States Patent [19]

Toussaint et al.

[11] Patent Number: 4,532,082
[45] Date of Patent: Jul. 30, 1985

[54] PREPARATION OF 3-CYANO-2-ALKYLALKANALS

[75] Inventors: Herbert Toussaint, Frankenthal; Hans J. Pander, Roedersheim-Gronau, both of Fed. Rep. of Germany

[73] Assignee: BASF Aktiengesellschaft, Fed. Rep. of Germany

[21] Appl. No.: 470,932

[22] Filed: Mar. 1, 1983

[30] Foreign Application Priority Data

Mar. 3, 1982 [DE] Fed. Rep. of Germany ....... 3207614

[51] Int. Cl.³ ................. C07C 120/02; C07C 121/34; C07C 121/36
[52] U.S. Cl. ................. 260/465.1; 260/465.6
[58] Field of Search ...................... 260/465.1

[56] References Cited

U.S. PATENT DOCUMENTS 2,565,537 8/1951 Warner et al. ............. 260/465.1
3,444,161 5/1969 Nagata .................. 260/239.55

OTHER PUBLICATIONS

Mathieu, et al.; "Formation of C—C Bonds", (1973), vol. 1, p. 396; George Thieme Publishers, Stuttgart.
Rossi, et al., C. A., 42 (1948), 4938i to 4939a.
Rossi, et al., Helvetica Chimica Acta, 31, (1948), pp. 486-487.
Houben-Weyl, "Methoden der Organischen Chemie", vol. 8, pp. 272-279 (1952).

Primary Examiner—Joseph Paul Brust
Attorney, Agent, or Firm—Keil & Weinkauf

[57] ABSTRACT

3-Cyanoaldehydes of the formula I

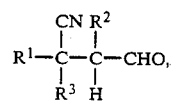

where $R^1$ and $R^2$ are each $C_1$–$C_6$-alkyl and $R^3$ is hydrogen or $C_1$–$C_3$-alkyl, are prepared by a process wherein an aldehyde of the formula II

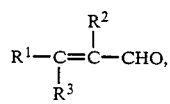

is reacted with anhydrous hydrocyanic acid in the presence of a basic catalyst, in a solvent.

4 Claims, No Drawings

PREPARATION OF 3-CYANO-2-ALKYLALKANALS

The present invention relates to a novel process for the preparation of aliphatic aldehydes which contain a cyano group in the 3-position.

Houben-Weyl, "Methoden der organischen Chemie", Vol. 8, page 272 et seq., discloses that 3-cyanoalkyl ketones can be obtained by an addition reaction of hydrocyanic acid with an α,β-unsaturated ketone, eg. methyl vinyl ketone, at elevated temperatures, while at low temperatures only the cyanohydrins are formed. According to this publication, a similar reaction of an α,β-unsaturated aldehyde with hydrocyanic acid gives exclusively a cyanohydrin, and the hydrogen cyanide does not undergo addition at the double bond. According to U.S. Pat. No. 2,565,537, this statement is qualified by the fact that an addition reaction of this type can in fact take place if acrolein, methacrolein or crotonaldehyde (ie. an unsaturated aldehyde which carries no more than one alkyl group in the α-position and β-position together), dissolved in a lower alcohol, is reacted with hydrocyanic acid in the course of 1 to 4 hours at from 50° to 100° C.

Finally, U.S. Pat. No. 3,444,161 discloses that an α,β-unsaturated carbonyl compound can be converted to a 3-cyanocarbonyl compound if the hydrocyanic acid is employed in the form of a cyano-aluminum complex. Even if they take place in a shorter time, these reactions are very troublesome to carry out, since the cyanoaluminum complex first has to be prepared in an additional operation.

It is an object of the present invention to prepare 3-cyanoaldehydes by a very simple process.

We have found that this object is achieved, and that 3-cyanoaldehydes of the general formula I

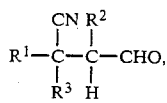

where $R^1$ and $R^2$ are identical or different and are each straight-chain or branched alkyl of 1 to 6 carbon atoms and $R^3$ is hydrogen or alkyl of 1 to 3 carbon atoms, are advantageously obtained, if an α,β-unsaturated aldehyde of the general formula II

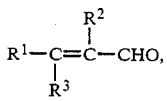

where $R^1$, $R^2$ and $R^3$ have the above meanings, if appropriate in a solvent, is mixed with hydrocyanic acid in the presence of from 0.01 to 1.0% by weight, based on the aldehyde, of a basic catalyst, and the reaction mixture is heated at from 100° to 200° C. for from 1 to 120 minutes.

In view of Houben-Weyl (see above) and U.S. Pat. No. 2,565,537, this reaction route has to be considered as surprising, since on the one hand the formation of a cyanohydrin was to be expected in any event, while on the other hand it was to be feared that at such high temperatures and in an alkaline medium an aldol condensation would take place as a competing reaction. This is pointed out in U.S. Pat. No. 2,565,537, according to which the amount of alkaline catalyst should be kept very low, even at the relatively low temperatures recommended therein, in order to avoid polymerization of the aldehyde.

Starting compounds for the 3-cyanoaldehydes prepared by the novel process are α,β-unsaturated aldehydes of the above formula II, where $R^1$, $R^2$ and $R^3$ have meanings conforming to the above definition. $R^1$ is preferably alkyl of 1 to 4 carbon atoms, $R^2$ is preferably alkyl of 1 to 3 carbon atoms and $R^3$ is preferably hydrogen, methyl or ethyl. The alkyl groups can be straight-chain or branched.

Specific examples of compounds of the formula II are 2-methylbut-2-enal, 2-methylpent-2-enal, 2-methylhex-2-enal, 2-methylhept-2-enal, 2-ethylbut-2-enal, 2-ethylpent-2-enal, 2-ethylhex-2-enal, 2-ethylhept-2-enal, 2-ethyl-5-methylhex-2-enal, 2,3-dimethylbut-2-enal and 2-propylhept-2-enal.

Such an aldehyde is, if appropriate, dissolved in a solvent, after which the basic catalyst is added in an amount of 0.01 to 1.0, preferably from 0.05 to 0.5, % by weight, based on the aldehyde.

For the purposes of the invention, solvents are strongly polar ones, eg. isobutanol, dimethylformamide, N,N-dimethylacetamide, N-methylpyrrolidone or dimethylsulfoxide. Advantageously, the amount of solvent should be such that the reaction solution contains from 10 to 90, preferably from 25 to 70, % by weight of aldehyde.

Examples of alkaline catalysts are quaternary ammonium bases, sodium hydroxide, potassium hydroxide and alkali metal alcoholates, such as methylates, ethylates, t-butylates or preferably sodium ethyleneglycolate, potassium ethyleneglycolate, sodium propyleneglycolate or potassium propyleneglycolate.

One embodiment comprises adding to the catalyst-containing aldehyde solution the amount of hydrocyanic acid required for the reaction, an equilibrium reaction initially taking place to give cyanohydrin. Preferably, hydrocyanic acid is employed in this process in slightly less than the molar amount, based on the aldehyde. However, it is also possible to dissolve previously prepared aldehyde cyanohydrin together with the catalyst in the solvent, the amount of the cyanohydrin being such that it corresponds to the above amount of aldehyde.

The solution thus obtained is then heated in a suitable reaction vessel at from 100° to 200° C., preferably from 120° to 160° C., for from 1 to 120, preferably from 5 to 40, minutes, and is thereafter cooled again very rapidly.

In another embodiment, the catalyst is added to a mixture of hydrocyanic acid, an aldehyde and if appropriate a solvent, and this reaction mixture is kept at the stated temperature for the stated time.

In order to achieve very exact heating and defined residence times, the process is preferably carried out continuously. To do this, for example, a catalyst-containing aldehyde cyanohydrin solution is passed continuously through a heated tubular reactor or over a reactor cascade. The residence time should be of the above duration, conforming to the definition; in general, a residence time of from 5 to 40 minutes is sufficient.

When the reaction is carried out under optimum conditions, yields as high as 90% of theory are obtained. The reaction solution is discharged from the reactor, a mineral acid, eg. phosphoric acid, is added to neutralize the basic catalyst, and the mixture is then worked up in a conventional manner.

This can be done, for example, by distillation under reduced pressure, a mixture of solvent and unreacted unsaturated aldehyde being first taken off as a low-boiling fraction. This mixture can be recycled to the reaction, if desired without further purification. For quantitative determination of the amount of aldehyde in the low-boiling fraction, an aliquot part is diluted with water, whereupon the unsaturated aldehyde separates out as an organic phase. The higher-boiling fraction obtained comprises the desired 3-cyanoaldehyde in high purity.

If solvents which have an unrestricted miscibility with water are employed for the reaction, the reaction solution may also be introduced into water which has been brought to an acidic pH in order to neutralize the basic catalyst. In this procedure, the solvent passes into the aqueous phase while the organic phase contains the cyanoaldehyde and unreacted unsaturated aldehyde. This phase, if appropriate after the addition of a water-insoluble solvent, is dried, and fractionally distilled under reduced pressure.

The above 3-cyanoaldehydes are useful intermediates which can be converted, for example by hydrogenation under conditions of amination, to 1,3-diamines; these in turn are used as reactants in the preparation of, for example, epoxide resin hardeners.

The Examples which follow illustrate the invention. Parts and percentages are by weight, unless expressly stated otherwise. Parts by volume bear the same relation to parts by weight as that of the liter to the kilogram.

EXAMPLE 1

195 parts of 97% strength 2-ethylhex-2-enal, 77 parts of N-methylpyrrolidone and 33 parts of stabilizer-free hydrocyanic acid were initially taken in a stirred autoclave. The autoclave was closed, 18 parts of a 5% strength solution of sodium hydroxide in ethylene glycol were then metered in over about 5 minutes, and the autoclave was then heated at 115° C. for 40 minutes. After the reaction was complete, the product was removed via a siphon tube, and introduced onto a mixture of 5 parts of 85% strength phosphoric acid and 300 parts of ice. The organic phase was taken up in 300 parts of diethyl ether, and the solution was washed with three times 500 parts of water, dried over magnesium sulfate and fractionally distilled. 55 parts of 2-ethylhex-2-enal and 117 parts of 3-cyano-2-ethylhexanal were obtained in a boiling range of from 35° to 47° C./0.05 mbar. This corresponded to a yield of 68.9% of theory, based on 2-ethylhex-2-enal converted, or 62.6% of theory, based on hydrocyanic acid employed.

EXAMPLE 2

303 parts of anhydrous gaseous hydrogen cyanide were passed into a solution of 1,820 parts of 97% strength 2-ethylhex-2-enal, 1,820 parts of N,N-dimethylacetamide and 12 parts of a 5% strength solution of sodium hydroxide in ethylene glycol, while cooling at 40° C. The resulting reaction mixture was employed for the continuous reaction described below.

553 parts per hour of the above reaction mixture and 8 parts per hour of a 5% strength solution of sodium hydroxide in ethylene glycol were metered into the first flask in a cascade of three stirred flasks, each of which had a reaction volume of 50 parts by volume and was capable of being heated. The average residence time was about 5 minutes per reactor. By means of two heating cycles, the internal temperature of the first flask was kept at 130° C., and the internal temperatures of the second and third flasks were kept at 140° C. The reaction mixture emerging from the third flask was cooled to 20°–30° C., 5 parts per hour of 85% strength phosphoric acid were added and the mixture was collected.

1,569 parts of the reacted mixture were taken up in 1,000 parts of diethyl ether, the solution was washed with three times 1,500 parts of water, the organic phase was dried over magnesium sulfate, the solvent was separated off under greatly reduced pressure and the residue was then distilled. 175 parts of unreacted 2-ethylhex-2-enal and 570 parts of 3-cyano-2-ethylhexanal of boiling point 45°–47° C./0.05 mbar were obtained. This corresponds to a yield of 92.3% of theory, based on 2-ethylhex-2-enal converted, or 85.7% of theory, based on hydrogen cyanide employed. According to gas chromatography, the product was 99.5% pure.

C: 70.4% (calculated: 70.59%); H: 9.9% (calculated 9.80%); N: 9.1% (calculated: 9.15%); O: 10.5% (calculated: 10.46%).

EXAMPLE 3

A compartment reactor comprising nine compartments, each of which has a capacity of 20 parts by volume, is capable of being heated via two separate oil cycles. Oil cycle 1 was adjusted to 120° C., and oil cycle 2 was adjusted to 150° C. A mixture of 235 parts per hour of 2-ethylhex-2-enal, 235 parts per hour of N,N-dimethylacetamide and 39 parts per hour of stabilizer-free hydrocyanic acid on the one hand, and 20 parts per hour of a 2.5% strength solution of sodium hydroxide in ethylene glycol on the other hand, were metered through the reactor via two separate pumps. The reaction mixture which emerged at the reactor exit was cooled to 70°–80° C., and 13 parts per hour of 85% strength phosphoric acid were added. The solution was passed over a thin-film vaporizer, which was operated at 140° C. and under a reduced pressure of 0.5 mbar. 343 parts per hour of distillate were obtained, comprising 51 parts of 2-ethylhex-2-enal, 153 parts of 3-cyano-2-ethylhexanal and 230 parts of N,N-dimethylacetamide. This corresponded to a yield of 71.3% of theory, based on unreacted 2-ethylhex-2-enal, or 69.2% of theory, based on hydrocyanic acid employed.

EXAMPLE 4

A mixture of 201 parts per hour of 2-methylpent-2-enal, 103 parts per hour of N-methylpyrrolidone and 45 parts per hour of stabilizer-free hydrocyanic acid on the one hand, and 15 parts per hour of a 5% strength solution of sodium hydroxide in ethylene glycol on the other hand, were metered separately, via two pumps, into the cascade of three stirred flasks which was described in Example 2. The average residence time was about 8 minutes per flask. By appropriate heating, the temperature in the reactors was kept at 120° C. The reaction mixture which emerged from the third stirred flask was cooled to 20°–30° C., and 4 parts per hour of 85% strength phosphoric acid were added.

761 parts of the reacted mixture were dissolved in 500 parts of diethyl ether, the solution was washed with three times 500 parts of water, and the organic phase which remained was dried over magnesium sulfate and fractionally distilled. After the diethyl ether had been separated off, 169 parts of 2-methylpent-2-enal and 192 parts of 3-cyano-2-methylpentanal of boiling point 95°–96° C./11 mbar were obtained. This corresponded to a yield of 61% of theory, based on 2-methylpent-2-enal converted, or 44.5% of theory, based on hydrocyanic acid employed.

C: 67.0%; calculated: 67.2%, H: 8.9%; calculated: 8.8%, N: 11.0%; calculated: 11.2%, O: 13.1%; calculated: 12.8%, Carbonyl number 438; calculated: 449.

EXAMPLE 5

351 parts of anhydrous gaseous hydrogen cyanide were passed into a solution of 1,812 parts of 2-methylhex-2-enal, 825 parts of N-methylpyrrolidone and 83 parts of a 5% strength solution of sodium hydroxide in ethylene glycol at from 35° to 40° C., while cooling. The resulting reaction mixture was employed for the continuous reaction described below.

378 parts per hour of the above reaction mixture were metered into a cascade which was capable of being heated and comprised three stirred flasks, each having a reaction volume of 50 parts by volume. The average residence time was about 8 minutes per reactor. The reaction temperature in the flasks was kept at 130° C. by separate heating cycles. The reaction mixture which emerged from the third flask was cooled, and 4 parts per hour of 95% strength phosphoric acid were added. 806 parts of the solution stabilized with phosphoric acid were taken up in 400 parts of methyl tert.-butyl ether, the ethereal solution was washed with three times 500 parts of water and dried over magnesium sulfate, the methyl tert.-butyl ether was separated off and the residue was distilled under reduced pressure. 217 parts of 2-methylhex-2-enal of boiling point 58°–59° C./15 mbar and 243 parts of 3-cyano-2-methylhexanal of boiling point 44°–45° C./0.1 mbar were obtained. This corresponded to a yield of 77.1% of theory, based on 2-methylhex-2-enal converted, or 51.8% of theory, based on hydrogen cyanide employed.

C: 68.8%; calculated: 69.06%, H: 9.4%; calculated: 9.35%, N: 10.4%; calculated: 10.07%, O: 11.8%; calculated: 11.51%, Carbonyl number 395; calculated: 403.7.

EXAMPLE 6

285 parts of gaseous hydrogen cyanide were passed into a mixture of 1,801 parts of 2-ethyl-5-methylhex-2-enal, 4,042 parts of N,N-dimethylacetamide and 250 parts of a 4.5% strength solution of potassium hydroxide in ethylene glycol at 40° C., while cooling. The resulting solution was employed for the continuous reaction described below.

1,058 parts per hour of the above reaction mixture were metered into the compartment reactor described in Example 3. Oil cycle 1 was adjusted to 130° C. and oil cycle 2 was adjusted to 150° C. The average residence time was 9.5 minutes. The mixture which emerged at the reactor exit was cooled to 20°–30° C., and 7 parts per hour of 85% strength phosphoric acid were added. 2,766 parts parts of the reaction mixture were filtered, and then distilled in a thin-film vaporizer at 140° C. and under a reduced pressure of 1 mbar. 2,623 parts of crude distillate and 143 parts of distillation residue were obtained, and the crude distillate was redistilled under greatly reduced pressure. 1,502 parts of a mixture of N,N-dimethylacetamide and 2-ethyl-5-methylhex-2-enal were obtained in a boiling range from 21°–25° C./0.5 mbar. When 3,000 parts of water were added to this mixture, it was possible to isolate 160 parts of 2-ethyl-5-methylhex-2-enal. 490 parts of 3-cyano-2-ethyl-5-methylhexanal were obtained at 55°–56° C./0.5 mbar, as the reaction product. This corresponded to a yield of 66.1% of theory, based on 2-ethyl-5-methylhex-2-enal converted, or 64.1% of theory, based on hydrogen cyanide employed.

C: 71.9%; calculated: 71.86%, H: 10.1%; calculated: 10.18%, N: 8.3%; calculated: 8.38%, O: 9.7%; calculated: 9.58%, Carbonyl number: calculated: 336.

EXAMPLE 7

308 parts of gaseous hydrogen cyanide were passed into a mixture of 1,775 parts of 2-methylhept-2-enal, 714 parts of N-methylpyrrolidone and 67 parts of a 5% strength solution of NaOH in ethylene glycol in the course of one hour at 40° C. The mixture was allowed to continue reacting for 15 minutes at 40° C., after which the resulting reaction solution was cooled and then employed for the continuous reaction described below.

372 parts per hour of the above reaction solution were metered into the cascade which consisted of three stirred flasks and was described in Example 2. By appropriate heating, the temperature in the three flasks was kept at 140° C. The average residence time was 8 minutes per reactor. The product which emerged from the third flask was cooled to about 30° C., 963 parts of the cooled product were taken up in 650 parts of diethyl ether, the solution was washed with three times 500 parts of water to which 2% of phosphoric acid had been added, the organic phase was dried over magnesium sulfate, the diethyl ether was distilled off and the crude product which remained was distilled in a thin-film vaporizer. 550 parts of distillate and 80 parts of residue were obtained. Fractional redistillation gave 285 parts of 2-methylhept-2-enal of boiling point 60°–62° C./13 mbar and 297 parts of 3-cyano-2-methylheptanal of boiling point 111°–112° C./13 mbar. This corresponded to a yield of 78.3% of theory, based on 2-methylhept-2-enal converted, or 50.6% of theory, based on hydrogen cyanide employed.

C: 70.7%; calculated: 70.59%, H: 10.0%; calculated: 9.80%, N: 9.3%; calculated: 9.15%, O: 10.3%; calculated: 10.46%, Carbonyl number: 366, calculated: 366.7.

EXAMPLE 8

205 parts of gaseous hydrogen cyanide were passed into a mixture of 1,454 parts of 2-propylhept-2-enal, 1,482 parts of N,N,-dimethylacetamide and 6 parts of a 4.8% strength solution of sodium hydroxide in ethylene glycol in the course of about one hour at 40° C. The reaction mixture was cooled to 20° C., 81 parts of a 4.8% strength solution of sodium hydroxide in ethylene glycol were added, and the mixture was then employed for the continuous reaction described below.

553 parts per hour of the catalyst-containing reaction solution were metered, via a pump, into the compartment reactor described in Example 3. Oil cycle 1 was adjusted to 140° C., and oil cycle 2 was adjusted to 160° C. The average residence time was 18 minutes. The mixture which emerged at the reactor exit and was at 155° C. was cooled to 30° C., and 5 parts per hour of 85% strength phosphoric acid were added. 1,581 parts of the reaction mixture were filtered, and the filtrate was distilled in a thin-film vaporizer at 140° C. and under 0.5 mbar to give 1,463 parts of a slightly yellow distillate, which was redistilled over a short column. 972 parts of a mixture of N,N-dimethylacetamide and 2-propylhept-2-enal of boiling point 22°–33° C./0.5 mbar were separated off, and 451 parts of 3-cyano-2-propylheptanal of boiling point 78°–79° C./0.5 mbar were then obtained. It was possible to recover 254 parts of unreacted 2-propylhept-2-enal from the first fraction by adding 1,200 parts of water. This corresponded to a yield of 84.9% of theory, based on unreacted 2-propylhept-2-enal, or 67.6% of theory, based on hydrogen cyanide employed.

C: 72.7%; calculated: 72.93%, H: 10.6%; calculated: 10.50%, N: 7.6%; calculated: 7.73%, O: 8.9%; calculated: 8.84%, Carbonyl number: 314; calculated: 310.

EXAMPLE 9

160 parts of freshly distilled hydrocyanic acid were added, a little at a time, to a mixture of 712 parts of 2,3-dimethylbut-2-enal, 1,424 parts of N,N-dimethylacetamide and 16 parts of a 1% strength solution of sodium hydroxide in ethylene glycol at 40° C., while cooling. The reaction mixture was cooled, 48 parts of a 4.8% strength solution of sodium hydroxide in glycol were added, and the mixture was then employed for the continuous reaction described below.

564 parts per hour of the above reaction mixture were metered, via a pump, into the compartment reactor described in Example 3. Oil cycle 1 of the reactor was adjusted to 120° C., and oil cycle 2 was adjusted to 150° C. The average residence time was 18 minutes. 5 parts per hour of 85% strength phosphoric acid were added to the product which emerged at the reactor exit.

854 parts of the reaction mixture were poured onto 1,000 parts of water. The oil which floated on the surface was taken up in 300 parts of diethyl ether, the aqueous phase was extracted further with twice 150 parts of diethyl ether, and the combined extracts were washed once with 200 parts of water, dried over magnesium sulfate and distilled. The solvent and unreacted 2,3-dimethylbut-2-enal were separated off, and 103 parts of 3-cyano-2,3-dimethylbutanal of boiling point 79°–80° C./13 mbar were then obtained. This corresponded to a yield of 59.4% of theory, based on hydrocyanic acid employed.

C: 67.1%; calculated: 67.20%, H: 8.6%; calculated: 8.80%, N: 11.3%; calculated: 11.20%, O: 12.9%; calculated: 12.80%.

We claim:

1. A process for the preparation of a compound of the formula I

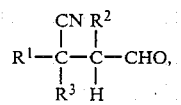

where $R^1$ and $R^2$ are identical or different and are each straight-chain or branched alkyl of 1 to 6 carbon atoms and $R^3$ is hydrogen or alkyl of 1 to 3 carbon atoms, wherein an unsaturated aldehyde of the formula II

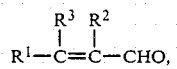

where $R^1$, $R^2$ and $R^3$ have the above meanings, is mixed with hydrocyanic acid in the presence of from 0.01 to 1.0% by weight, based on the aldehyde, of a basic catalyst, and the reaction mixture is heated at from 100° to 200° C. for from 1 to 120 minutes.

2. A process as claimed in claim 1, wherein the aldehyde is reacted with hydrocyanic acid to give a cyanohydrin as the initial product, and this is heated in the presence of the catalyst, in the solvent.

3. A process as claimed in claim 2, wherein the reaction is carried out continuously.

4. A process as claimed in claim 1, wherein the reaction is carried out in a solvent.

* * * * *